US00PP23472P2

(12) United States Plant Patent
Blom

(10) Patent No.: US PP23,472 P2
(45) Date of Patent: Mar. 12, 2013

(54) ***ECHINACEA* PLANT NAMED 'WHITE DOUBLE DELIGHT'**

(50) Latin Name: *Echinacea hybrida*
Varietal Denomination: White Double Delight

(76) Inventor: Arie Blom, Oudewater (NL)

( * ) Notice: Subject to any disclaimer, the term of this patent is extended or adjusted under 35 U.S.C. 154(b) by 106 days.

(21) Appl. No.: 13/068,697

(22) Filed: May 17, 2011

(51) Int. Cl.
*A01H 5/00* (2006.01)

(52) U.S. Cl. ..... Plt./428
(58) Field of Classification Search ..... Plt./428
See application file for complete search history.

*Primary Examiner* — June Hwu
(74) *Attorney, Agent, or Firm* — C. A. Whealy

(57) ABSTRACT

A new and distinct cultivar of *Echinacea* plant named 'White Double Delight', characterized by its upright plant habit; moderately vigorous growth habit; freely basal branching habit; strong flowering stems; early and freely flowering habit; long flowering period; large anemone-type inflorescences with white-colored ray and yellow green-colored disc florets; and good garden performance.

2 Drawing Sheets

Botanical designation: *Echinacea hybrida.*
Cultivar denomination: 'WHITE DOUBLE DELIGHT'.

BACKGROUND OF THE INVENTION

The present invention relates to a new and distinct cultivar of *Echinacea* plant, botanically known as *Echinacea hybrida*, and hereinafter referred to by the name 'White Double Delight'.

The new *Echinacea* plant is a naturally-occurring branch mutation of *Echinacea hybrida* 'Pink Double Delight', disclosed in U.S. Plant Pat. No. 18,803. The new *Echinacea* plant was discovered and selected by the Inventor on a single flowering plant within a population of plants of 'Pink Double Delight' grown in a controlled greenhouse environment in Zuidwolde, The Netherlands in July, 2007.

Asexual reproduction of the new *Echinacea* plant by micropropagation a controlled environment in Heerhugowaard, The Netherlands since August, 2007, has shown that the unique features of this new *Echinacea* plant are stable and reproduced true to type in successive generations.

SUMMARY OF THE INVENTION

Plants of the new *Echinacea* have been observed under all possible environmental conditions and cultural practices. The phenotype may vary somewhat with variations in environment such as temperature and light intensity, without, however, any variance in genotype.

The following traits have been repeatedly observed and are determined to be the unique characteristics of 'White Double Delight'. These characteristics in combination distinguish 'White Double Delight' as a new and distinct *Echinacea* plant:

1. Upright plant habit.
2. Moderately vigorous growth habit.
3. Freely basal branching habit.
4. Strong flowering stems.
5. Early and freely flowering habit.
6. Large anemone-type inflorescences with white-colored ray and yellow green-colored disc florets.
7. Good garden performance.

Plants of the new *Echinacea* can be compared to plants of the parent selection. Plants of the new *Echinacea* differ primarily from plants of the parent selection in floret color as plants of the parent selection have pink-colored ray and disc florets.

Plants of the new *Echinacea* can be compared to plants of *Echinacea hybrida* 'Avalanche', disclosed in U.S. Plant Pat. No. 18,597. In side-by-side comparisons, plants of the new *Echinacea* differed from plants of 'Avalanche' primarily in the following characteristics:

1. Plants of the new *Echinacea* had lighter green-colored leaves than plants of 'Avalanche'.
2. Plants of the new *Echinacea* and 'Avalanche' differed in inflorescence form.

BRIEF DESCRIPTION OF THE PHOTOGRAPHS

The accompanying photographs illustrate the overall appearance of the new *Echinacea* plant showing the colors as true as it is reasonably possible to obtain in colored reproductions of this type. Colors in the photographs may differ slightly from the color values cited in the detailed botanical description which accurately describe the colors of the new *Echinacea* plant.

The photograph on the first sheet comprises a side perspective view of a typical flowering plant of 'White Double Delight' grown in a container.

The photograph at the top of the second sheet is a close-up view of a typical inflorescence of 'White Double Delight'.

The photograph at the bottom of the second sheet is a close-up view of the upper surface of a typical leaf of 'White Double Delight'.

DETAILED BOTANICAL DESCRIPTION

The aforementioned photographs and following observations and measurements describe plants grown during the late summer in an outdoor nursery in Zuidwolde, The Netherlands and under conditions and practices which approximate those generally used in commercial *Echinacea* production. During the production of the plants, day temperatures ranged from 12° C. to 24° C. and night temperatures ranged from 4° C. to 16° C. Measurements and numerical values represent averages for typical flowering plants. Plants were three and six months old when the photographs and description, respectively, were taken. In the following description, color references are made to The Royal Horticultural Society Colour Chart, 2007 Edition, except where general terms of ordinary dictionary significance are used.

Botanical classification: *Echinacea hybrida* 'White Double Delight'.

Parentage: Naturally-occurring branch mutation of *Echinacea hybrida* 'Pink Double Delight', disclosed in U.S. Plant Pat. No. 18,803.

Propagation:

*Type*.—By micropropagation.

*Time to initiate roots, summer*.—About one week at 25° C.

*Time to produce a rooted young plant, summer*.—About five weeks at 21° C.

*Root description*.—Fine, fibrous; pale cream in color.

*Rooting habit*.—Freely branching; moderately dense.

Plant description:

*Plant form/growth habit*.—Herbaceous perennial; upright and columnar plant habit, narrow inverted triangle; freely basal branching habit; moderately vigorous growth habit.

*Plant height*.—About 62.4 cm.

*Plant diameter or spread*.—About 35.1 cm.

*Basal branches*.—Length: About 46.4 cm. Diameter: About 3.5 mm. Internode length: About 6 cm. Aspect: Erect to about 20° from vertical. Strength: Strong. Texture: Sparsely pubescent, strigose; rough. Color: Close to 144C.

Foliage description:

*Arrangement*.—Alternate, simple.

*Length*.—About 11.7 cm.

*Width*.—About 3.9 cm.

*Shape*.—Narrowly ovate to ovate.

*Apex*.—Narrowly acute.

*Base*.—Long attenuate to narrowly cuneate.

*Margin*.—Entire; undulate; lower leaves shallowly serrate.

*Texture, upper and lower surfaces*.—Pubescent, strigose; rough.

*Venation pattern*.—Pinnate.

*Color*.—Developing leaves, upper surface: Close to 137B. Developing leaves, lower surface: Close to 137C. Fully expanded leaves, upper surface: Close to 147A; venation, close to 145B to 145C. Fully expanded leaves, lower surface: Close to 146A; venation, close to 145C.

*Petioles*.—Length: About 3.8 cm. Diameter: About 2 mm. Texture, upper surface: Smooth, glabrous. Texture, lower surface: Sparsely pubescent, strigose. Color, upper surface: Close to 144A. Color, lower surface: Close to 144C.

Inflorescence description:

*Appearance*.—Rotate anemone-type inflorescence form with ray and disc florets arranged acropetally on a capitulum; inflorescences positioned upright above the foliar plane on strong peduncles.

*Quantity of inflorescences per plant*.—About twelve.

*Fragrance*.—None detected.

*Time to flower*.—Plants flower continuously from early July to late September in The Netherlands.

*Inflorescence longevity*.—Inflorescences maintain good substance for about three weeks on the plant; inflorescences not persistent.

*Inflorescence bud*.—Height: About 2 cm. Diameter: About 1.7 cm. Shape: Oblong. Color: Close to 146A to 146B.

*Inflorescence size*.—Diameter: About 7.8 cm. Depth (height): About 3.5 cm. Disc diameter: About 5.1 cm. Receptacle height: About 8 mm. Receptacle diameter: About 1.2 cm. Receptacle color: Between 155C and 157D.

*Ray florets*.—Length: About 3.7 cm. Width: About 8 mm. Shape: Narrowly oblanceolate. Apex: Praemorse. Base: Cuneate. Margin: Entire. Texture, upper and lower surfaces: Smooth, glabrous; longitudinally ridged. Number of ray florets per inflorescence: About 17 arranged in a single whorl. Aspect: Horizontal to slightly drooping, about 20° from horizontal. Color: When opening, upper surface: Between 150D and 155A, but closest to 150D; apex, close to 145C to 145D; base, close to 145C. When opening, lower surface: Close to 150D; apex, close to 145B to 145C; base, close to 145C. Fully opened, upper surface: Between 150D and 155A, but closest to 155A; apex, close to 145C to 145D; base, close to 145C. With development, color becoming closer to 150D; apex, close to 145C; base, close to 145A. Fully opened, lower surface: Close to 150D; apex, between 145C and 150C; base, close to 145C. With development, color becoming closer to between 150D and 151D; apex and base, close to 144C to 144D.

*Disc florets*.—Length: About 1.8 cm. Diameter: About 9 mm. Shape: Tubular, enlarged; apices pointed. Number of disc florets per inflorescence: About 200. Texture, upper and lower surfaces: Smooth, glabrous. Color: Immature, inner and outer surfaces: Close to 145C; apex and base, close to 145B. Mature, inner and outer surfaces: Close to 145D; apex, close to 157D; base, close to 145B.

*Receptacle spines*.—Quantity: One per disc floret. Shape: Acicular. Apex: Acute. Base: Attenuate. Texture: Smooth, glabrous. Color: Apex: Close to 14A. Mid-section: Close to 144B. Base: Close to 145B.

*Involucral bracts*.—Quantity per inflorescence: About 60 arranged in about two whorls. Length: About 7 mm. Width: About 2 mm. Shape: Ovate. Apex: Acute. Base: Cuneate. Margin: Entire. Texture, upper surface: Smooth, glabrous. Texture, lower surface: Moderately pubescent; along the margins, densely pubescent. Color, upper surface: Close to 137A. Color, lower surface: Close to 137B.

*Peduncles*.—Length, terminal peduncle: About 12.7 cm. Diameter: About 4 mm. Strength: Strong. Aspect: Upright to about 25° from vertical. Texture: Sparsely pubescent, strigose. Color: Between 144C and 145B.

*Reproductive organs*.—Androecium (present on disc florets only): Quantity per floret: About four. Filament length: About 2 mm. Filament color: Close to 151D. Anther shape: Narrowly oblong. Anther length: About 2 mm. Anther color: Close to N199A to N199B. Pollen amount: Scarce. Pollen color: Greyed yellow. Gynoecium (present on ray and disc florets): Quantity per floret: One. Pistil length: About 6 mm. Stigma shape: Decurrent. Stigma color: Close to 144C. Style length: About 5 mm. Style color: Close to N144B. Ovary color: Close to 157A to 157B. Fruits/seeds: Fruit and seed development have not been observed.

Disease/pest resistance: Plants of the new *Echinacea* have not been shown to be resistant to pathogens and pests common to *Echinacea*.

Garden performance: Plants of the new *Echinacea* have exhibited good garden performance and tolerate rain and wind. Plants of the new *Echinacea* have been observed to tolerate high temperatures of about 35° C. and hardy to USDA Hardiness Zone 4.

It is claimed:

1. A new and distinct *Echinacea* plant named 'White Double Delight' as illustrated and described.

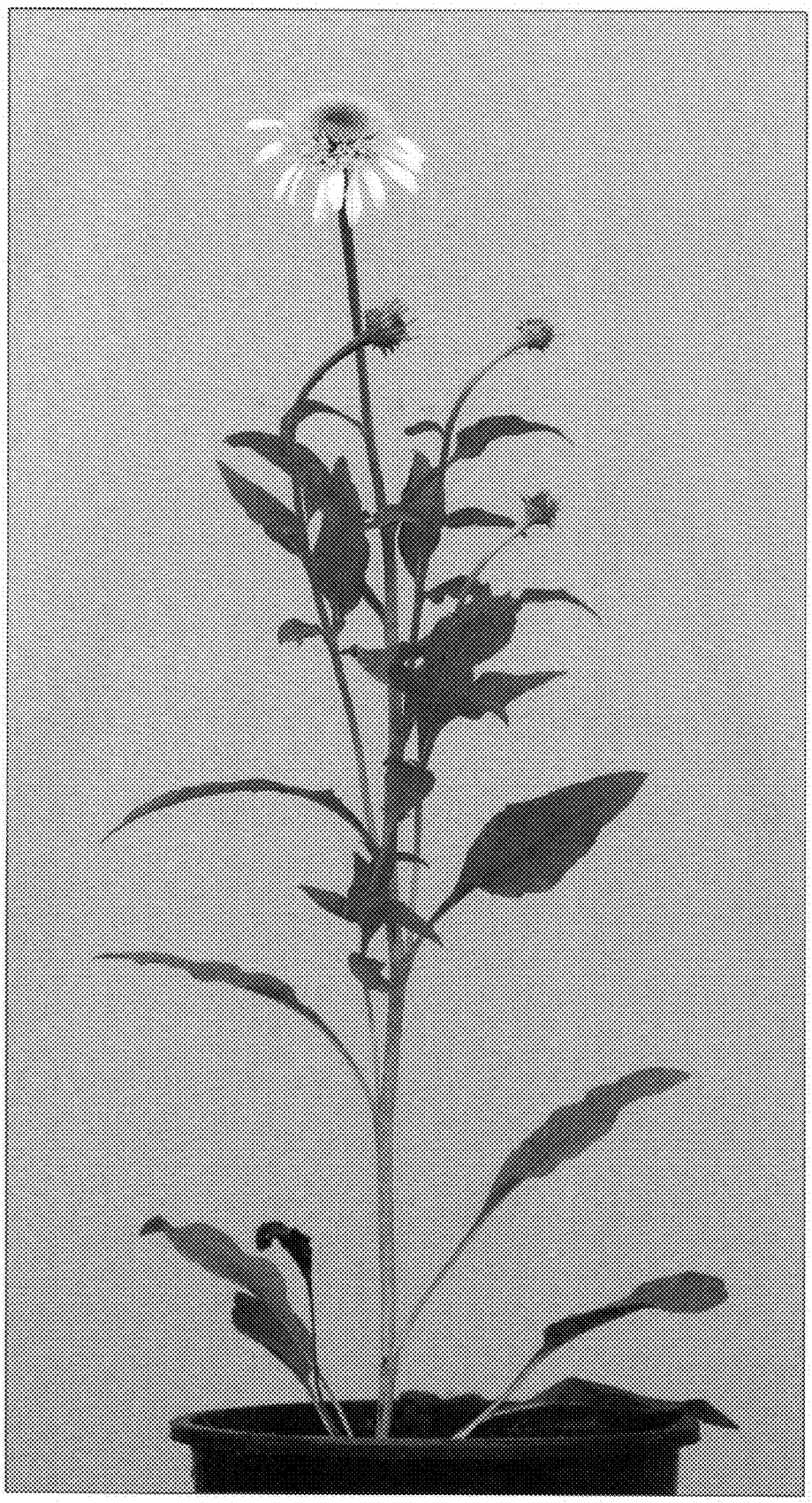

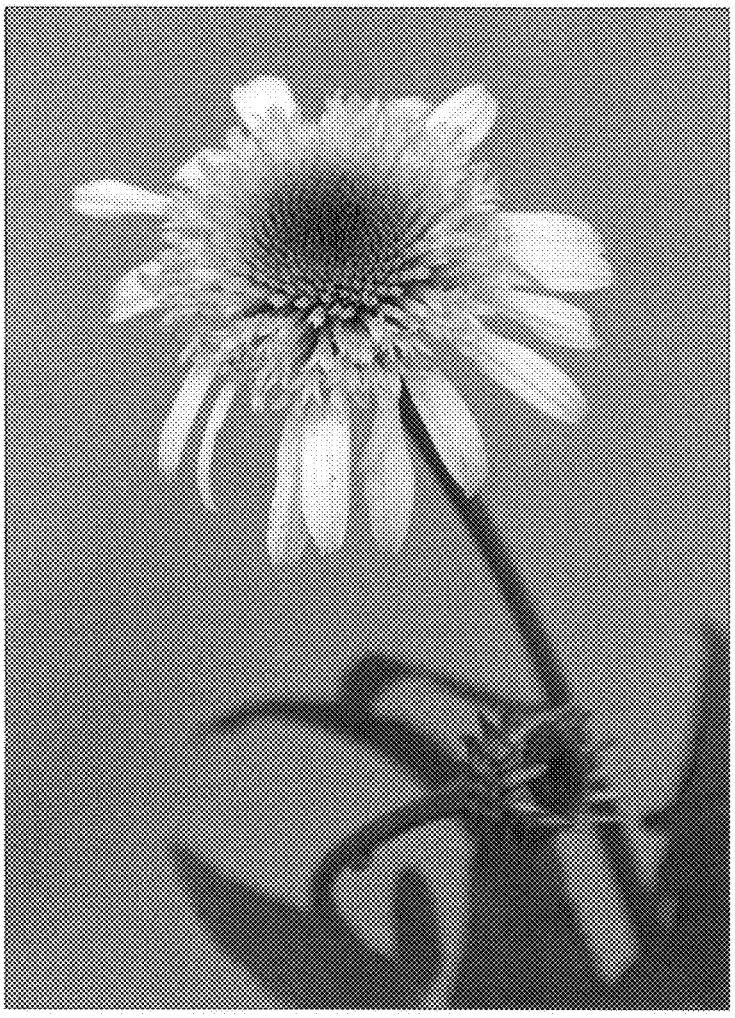
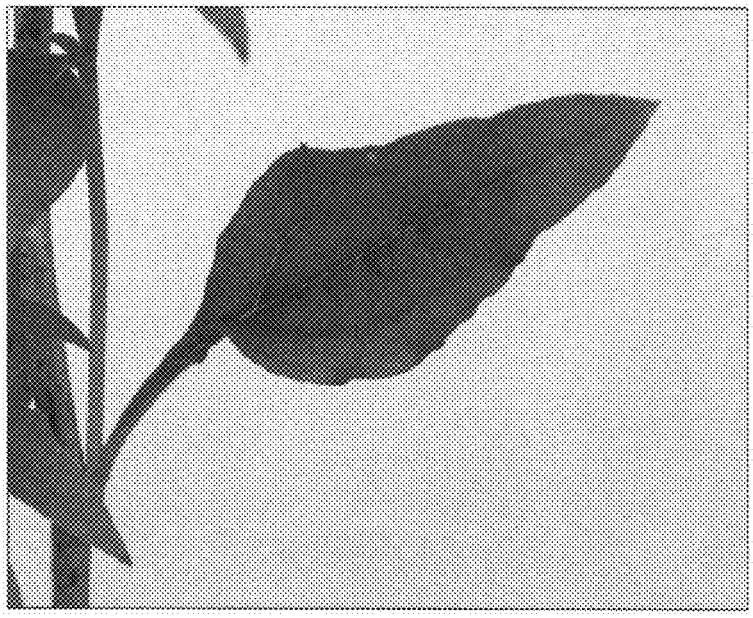

* * * * *